US006314796B1

(12) United States Patent
Wittekind et al.

(10) Patent No.: US 6,314,796 B1
(45) Date of Patent: Nov. 13, 2001

(54) METHOD AND DEVICE FOR NONDESTRUCTIVELY TESTING FLUID-FILLED CONTAINERS FOR LEAKTIGHTNESS

(75) Inventors: Juergen Wittekind, Frankfurt am Main; Gerhard Poss, Schriesheim; Andreas Kuehnel, Oberursel, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/319,805

(22) PCT Filed: Nov. 26, 1997

(86) PCT No.: PCT/EP97/06580

§ 371 Date: Aug. 2, 1999

§ 102(e) Date: Aug. 2, 1999

(87) PCT Pub. No.: WO98/26265

PCT Pub. Date: Jun. 18, 1998

(30) Foreign Application Priority Data

Dec. 10, 1996 (DE) .............................................. 196 51 208

(51) Int. Cl.[7] .............................. G01R 31/12; G01M 3/40; G01N 33/00; G01N 27/70
(52) U.S. Cl. ................................ 73/49.2; 73/52; 73/40.7; 324/536; 356/313
(58) Field of Search ................................. 73/49.2, 52, 40, 73/40.7, 705; 250/426; 324/462, 536, 464, 470, 559, 718; 356/313, 317, 72

(56) References Cited

U.S. PATENT DOCUMENTS

| | | | |
|---|---|---|---|
| 3,252,572 | * | 5/1966 | Erren ........................................ 209/81 |
| 4,125,805 | * | 11/1978 | Nagamatsu et al. .................... 324/54 |
| 4,677,372 | * | 6/1987 | Meguro et al. ......................... 324/54 |
| 4,788,850 | * | 12/1988 | Buschor et al. ....................... 73/49.2 |
| 5,128,269 | * | 7/1992 | Oitate et al. ........................... 436/126 |
| 5,198,773 | * | 3/1993 | Latta ..................................... 324/464 |
| 5,455,507 | * | 10/1995 | Horenstein ............................ 324/557 |
| 5,510,718 | * | 4/1996 | Enderby ................................ 324/536 |
| 5,535,618 | * | 7/1996 | Konieczka ............................ 73/49.3 |
| 5,537,859 | * | 7/1996 | Nakagawa ................................ 73/52 |
| 5,824,882 | * | 10/1998 | Griebel et al. ........................... 73/38 |
| 5,912,561 | * | 6/1999 | Mack ..................................... 324/718 |
| 6,009,744 | * | 1/2000 | Kovalchick et al. ..................... 73/40 |

* cited by examiner

*Primary Examiner*—Hezron Williams
*Assistant Examiner*—David J. Wiggins
(74) *Attorney, Agent, or Firm*—R. P. Raymond; M-E. M. Devlin; T. X. Witkowski

(57) ABSTRACT

Apparatus and process for non-destructively testing a fluid-filled container for leaktightness, the process comprising:

Figure 1:
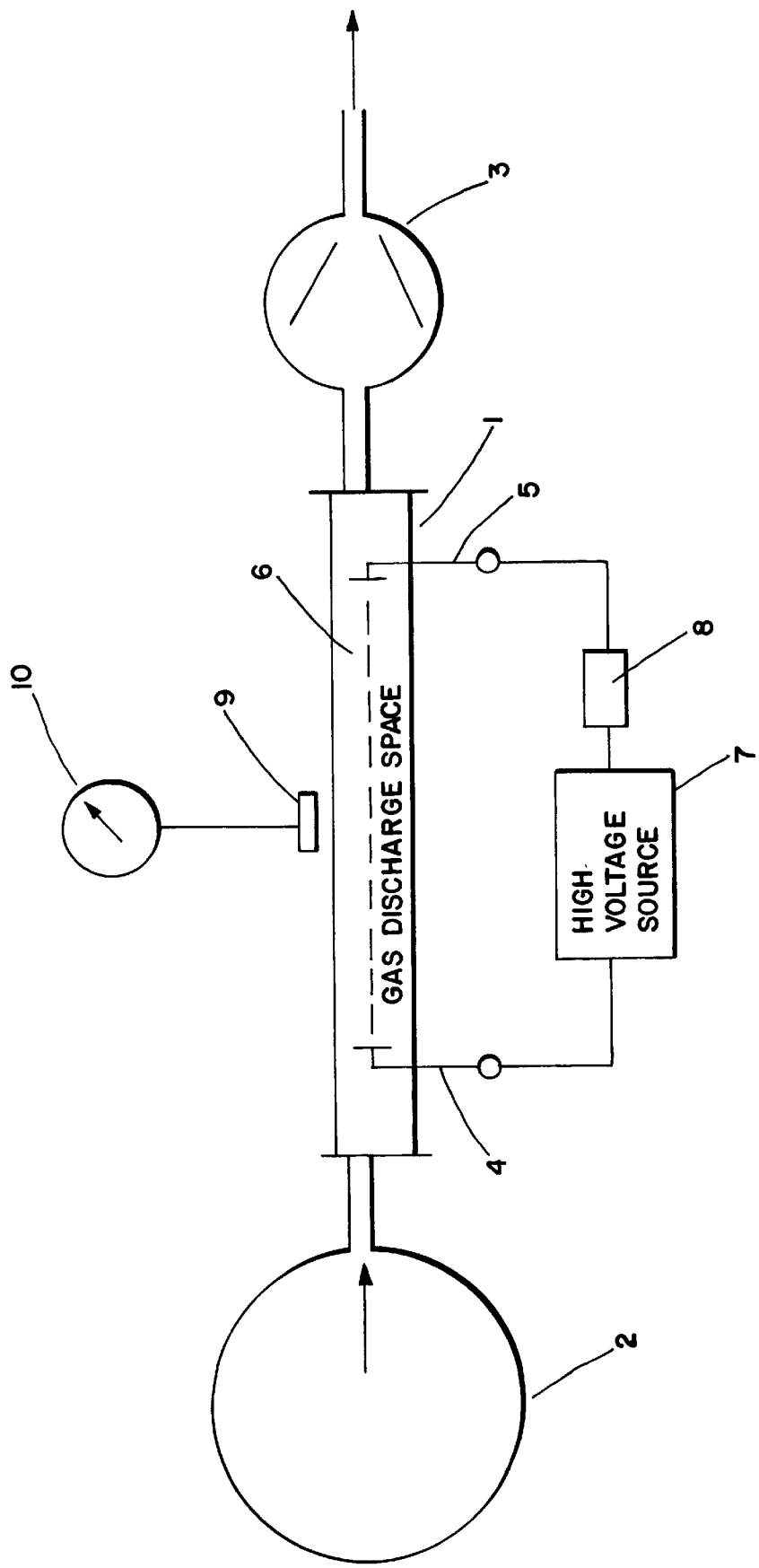

(a) subjecting the fluid-filled container to a vacuum or near vacuum environment;
(b) utilizing electrical equipment to form an electrical discharge in the vacuum or near vacuum environment sufficient to stimulate spectral light emissions from volatile fluid-filled container contents present in the vacuum or near vacuum environment;
(c) detecting the spectral light emissions from the volatile fluid-filled container contents produced in step (b); and
(d) evaluating the spectral light emissions detected in step (c) to determine the amount of volatile fluid-filled container contents present in the vacuum or near vacuum environment by comparing: (i) the measured brightness level of the spectral light emissions obtained from step (c), to (ii) a base brightness level obtained by measuring the brightness level of the spectral emissions due to the presence of residual gas or air molecules in the vacuum or near vacuum environment, and analyzing the difference between the measured brightness level and the base brightness level using a corresponding empirically-determined calibration curve of brightness level to concentration of volatile container contents.

24 Claims, 4 Drawing Sheets

METHOD AND DEVICE FOR NONDESTRUCTIVELY TESTING FLUID-FILLED CONTAINERS FOR LEAKTIGHTNESS

The invention relates to a process for non-destructively testing fluid-filled containers for leaktightness. Furthermore, the invention relates to a corresponding apparatus for non-destructively testing fluid-filled containers for leaktightness.

It is necessary to test the leaktightness of fluid-filled containers in many fields of technology, for example in the field of pharmacology. In this case, the container can be the cartridge of an item of pharmacological packaging, especially a cartridge for a propellant-free dosage aerosol.

Such cartridges have hitherto evaded an economic test for leaktightness.

Such a container for propellant-free application of a dosed quantity of a liquid medicament as a spray for inhalative application is described in international patent application WO 91/14468. The medicament solution is located in an exchangeable container which has a rigid outer container and a flexible inner container. An exactly-dosed quantity of the active ingredient solution is transferred from this container into a pumping chamber, and is there sprayed at high pressure through a small jet, wherein the particles which are formed are inhaled by the patient. Suitable containers are, for example, described in European patent document 532873. The advantage of this double-walled container is that the medicament solution can be removed without air or gas bubbles entering the inner container. Pressure compensation takes place by the inner flexible container collapsing upon itself whilst the rigid outer container provides protection from mechanical damage. The outer container contains openings for pressure compensation. If larger quantities of air or gas residue was to collect in the inner container, exact and reproducible individual dosage would no longer be guaranteed in the case of each individual application. A leak in the inner container, the walls of which comprise a very thin extruded foil, would result in gas and air bubbles forming during use, and possibly leading to a lower quantity of active ingredient solution being inhaled. In order to attain the greatest possible safety, it is thus necessary to test the container which is filled with the highly-effective medicament solution as to whether there is a leak in the inner container.

An economic test for leaktightness has hitherto not been found for this type of cartridge.

In order to detect traces of volatile materials, principally highly-sensitive sensors such as e.g. the flame ionisation detector or the photo ionisation detector are used in a known manner. However, these sensors are dependent on a gas atmosphere of at least atmospheric pressure; direct measurement in a vacuum is thus not possible. However, in order to be able to test the leaktightness of a container filled with a fluid, it must be brought into a vacuum so that a sufficient quantity of volatile material will be available for detection in the case of a leak. Furthermore, it is not possible to detect water traces in a gas atmosphere at a pressure below that of atmospheric pressure with any hitherto-known sensor.

It is also known, in gas analysis technology, to test the gas to be analysed emission-spectometrically, wherein the gas to be analysed is ionised by means of a constant high frequency discharge, in an evacuated gas discharge room, the pressure of which is between 0.01 and 5 Torr, i.e. a plasma is created wherein the light given off is spectrally decomposed and the intensities of the spectral lines which are characteristic of the ionised gases are photo-electrically measured (German patent specification 1 124 734). Similar processes and devices for gas analysis are shown in the document by Koch et al., "Über ein neuen Verfahren zur spektralen Gasanalyse", in Angewandte Chemie, 71, 1959, pages 545–549; GB 2 185 573 A; DE 195 05 104 A1; German patent document 1 087 832; U.S. Pat. No. 3,024,745 and DE-OS 1 598 303.

However, these known processes and devices are based on the analysis of supplied analysis gas through a spectral analysis, and not on the test for leaktightness of containers filled with fluid.

The objective of the invention is to specify a process and an apparatus for non-destructively testing fluid-filled containers for leaktightness, which allows a leak to be detected with greater precision and in a simple manner.

The solution of this objective takes place according to the invention for the process with the following steps:

provision of the containers filled with fluid in a vacuum,
undertaking of a gas discharge in the vacuum,
recording of the light emissions emanating from the gas discharge, and
evaluation of the light emissions for changes caused by volatile container contents exiting the tested containers as a result of a leakage.

With regard to the apparatus, the solution of the objective, according to the invention, succeeds with:

a receptacle in which a pressure beneath that of atmospheric pressure can be maintained and in which the containers which are to be examined are kept,
a gas discharge space in a vessel connected to the receptacle and electrical apparatus for effecting the gas discharge,
a light-sensitive sensor arrangement for recording the light emitted by the gas discharge, and
an evaluation circuit for evaluating the emitted light for changes caused by volatile container contents exiting the tested containers as a result of a leakage.

If there is a leakage in the containers, a small quantity of the container contents evaporates due to the vacuum, wherein the gas discharge undertaken between two electrodes detects both a change in brightness and a change in the spectral composition of the light emitted by the gas discharge as a result of these traces of material. Indeed, this effect does remind one of the known methods of atomic spectrometry, where the light emission of elements driven from a plasma at high power and at atmospheric pressure are used for detection of these elements; however, the detection of compounds, especially of organic compounds, is not possible in a vacuum with this method of atomic spectrometry. In addition to this, the testing of containers filled with fluid at atmospheric pressure for leaktightness is practically not possible.

For example, the methodology of atomic spectrometry is described in:

Hoffmann, H. J., Röhl, R: "Plasma-Emissions-Spectrometrie".
Analytiker Taschenbuch Vol. 5, pages 69–92, Springer-Verlag (1985), and
Brockaert, J. A. C., Schickling, C., Bings, N: "Mikrowellenplasmen für die Atomspektrometrie—Entwicklungsstand und analytische Anwendungen". GIT Fachz. Lab. 4/96, pages 323–37.

The influence of the volatile container contents on the light emission of the gas discharge is especially clear when, according to an embodiment of the invention, the provision of the containers and the activation of the gas discharge takes place at a pressure of between 0.05 and 50 mbar, preferably at a pressure of between 1 and 4 mbar.

Furthermore, according to a further feature of the invention, it is necessary for the leaktightness test for the gas discharge to be carried out by high-tension electrical energy which is supplied capacitively or inductively or by means of electrodes.

Especially good results can be attained if the gas discharge is activated at high voltage, which can be a DC or AC voltage with a frequency of greater than 50 Hz, preferably from 30–40 kHz.

Evaluation of the light emission can be made according to various viewpoints. One way, according to a further embodiment of the invention, is that the reduction of the brightness of the light emitted by the gas discharge compared to the basic brightness with the mere presence of the residual gas molecules of air in a vacuum is recorded, and this change in brightness is evaluated in connection with a corresponding empirically-determined calibration curve with regard to the concentration of the respective volatile container contents.

Another way, according to an embodiment of the invention, is that the change in the wavelength of the light emitted from the gas discharge is determined and analysed with regard to the type of the volatile container contents.

Other embodying features of the invention, especially with regard to the apparatus according to the invention, are subject of the subordinate claims and result from the embodiment examples represented in the drawings and from the subsequent description.

Figure 2:
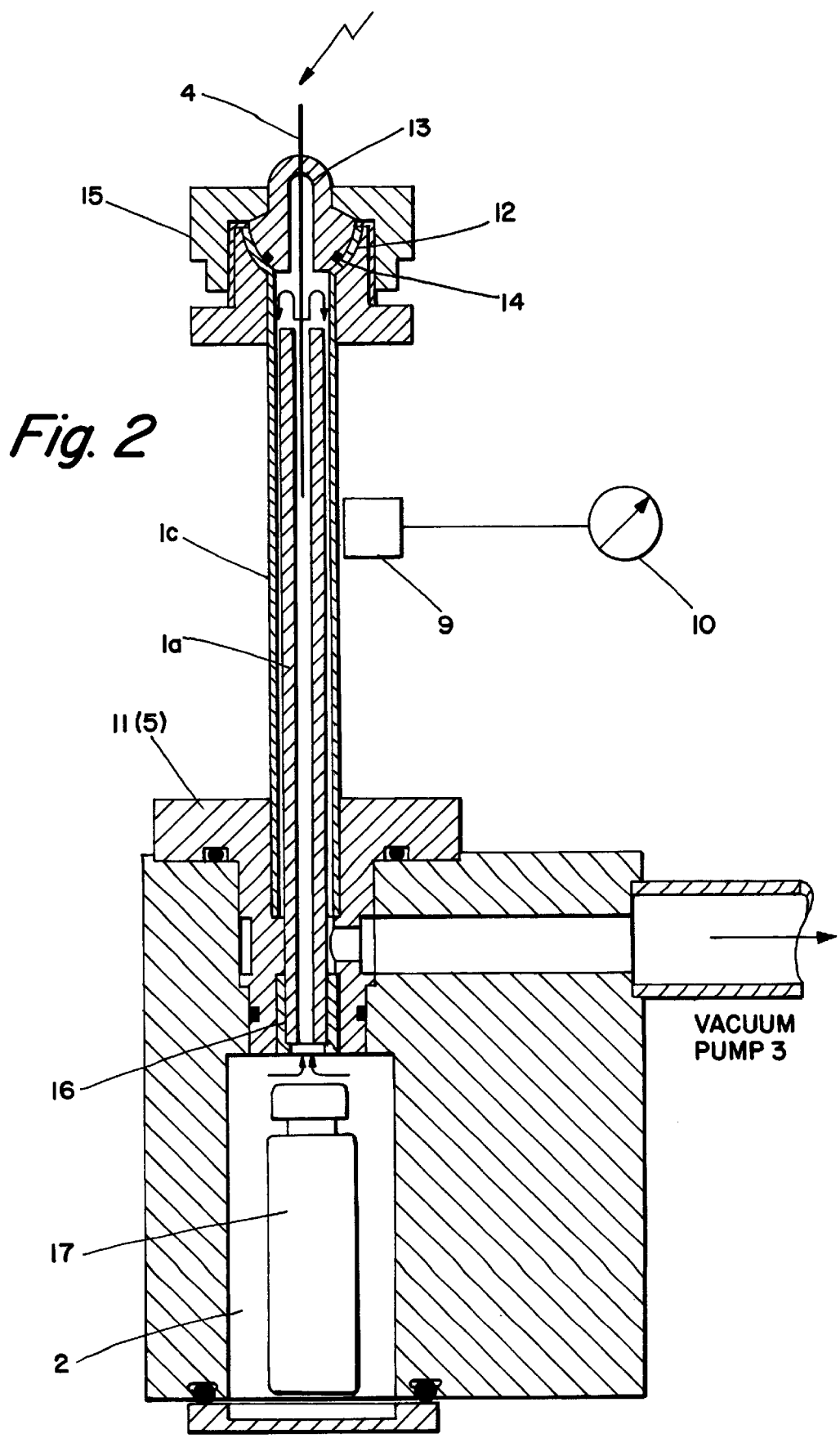

The following are shown:

FIG. 1 a first embodiment example of an apparatus according to the invention with a straight pipe for the gas discharge space, FIG. 1$a$ a derivation with a tube bent into a U-shape for the gas discharge space, FIG. 1$b$ a derivation with a spiral tube for the gas discharge space, and FIG. 2 a second embodiment example of an apparatus according to the invention with a coaxial tube system for the gas discharge space.

FIG. 1 shows an apparatus for non-destructively testing fluid-filled containers for leaktightness with a vessel in the form of a tube 1, which is made of a transparent material, e.g. quartz or glass. A reduced pressure with regards to the atmospheric pressure, a vacuum, can be maintained in this tube. To this end, it is placed between a receptacle 2 and a vacuum pump 3. The filled containers which are to undergo the leaktightness test are placed in the receptacle 2 (and hence in the vacuum), wherein in the case of leakages, traces of the filled container contents would also be detected in the vessel 1 in a manner which is still to be described.

Two high-voltage electrodes 4,5 are placed in the vessel 1, between which a gas discharge space 6 can be formed. A high-voltage source 7 is provided to activate the gas discharge space 6, which feeds high-voltage electrical energy into the gas discharge space via electrodes 4,5. The applied high voltage can either be DC voltage or a low-frequency AC voltage or a high-frequency AC voltage, wherein it has proven the case that the emitted brightness is less dependent on the residual gas pressure in the tube with increasing frequency. Frequencies in the range from 30–40 kHz have proven especially favourable, since interference radiation does not yet occur at these frequencies.

In order to limit the current flying across the gas discharge, a compensating resistance 8 is placed in the circuit which can also be formed by an impedance coil or a transformer with a large magnetic stray field. Laminar outer electrodes can also be provided in place of the electrodes 4,5 which are used.

The high-voltage electrical energy can also be supplied to the gas discharge space capacitively or inductively instead of via electrodes.

Furthermore, the apparatus according to the invention has a light-sensitive sensor arrangement, a photo sensor 9, to record the light emitted by the gas discharge. The photo sensor can be, for example, a photo resistance, a photo diode or a photo cell.

An evaluation stage 10 is connected in the circuit after the photo sensor 9 which serves to evaluate the emitted light for changes resulting from traces of the container contents. In the simplest case, the evaluation stage is a measuring instrument for measuring the brightness-dependent electrical signal of the photo sensor. It can also be formed by a microprocessor.

If a high voltage is applied to the electrodes 4,5, at reduced pressure, the residual gas molecules in the interior of the tube will be stimulated to light up between the electrodes in the form of a gas discharge, wherein the wavelength of the emitted light is determined by the type of the residual gas molecules or—in the case of noble gases—the gas atoms, whilst the brightness is determined by the pressure in the tube and the magnitude of the electrical voltage.

This process has been known for a long time and is used widely, for example, in neon advertisement tubes. However, the invention has its basis in the effect that both the brightness and the wavelength of the omitted light can be significantly altered by traces of volatile compounds.

It has been found that in the case of the presence of volatile organic or inorganic materials issuing from a leak in the filled containers, even in the smallest quantities, the gas discharge takes on a significant reduction in brightness in comparison to the brightness as displayed in the starting situation when only the residual gas molecules of air are present in the tube 1. This change in brightness is proportional to the concentration of volatile container contents, so that by means of an empirically-prepared calibration curve a direct statement on the concentration of the respective materials can be made.

Furthermore, a change in the wavelength of the emitted light goes along with the change in brightness, so that statements are also possible as to the type of the volatile material.

If air is present as residual gas molecules in the vacuum, that is predominantly nitrogen and oxygen, then the gas discharge emits a red/blue light; if, for example, traces of ethanol were brought into the vacuum, the light emission moves to the short-wave range with a light blue colouring and a high radiation proportion in the near UV range. If there are water traces in the vacuum, the gas discharge has a dark red colour with radiation proportions in the IR range.

In both cases, the emission in the visible range is significantly reduced.

In order to measure the changes in brightness of the emitted light, a photo sensor 9 is preferably used which is wavelength-independent in a wide range of the light spectrum. In order to detect the presence of a certain, pre-specified material, one expediently uses a photo sensor 9 which has a specific sensitivity maximum adapted to the type of material at a specified wavelength. A plurality of such photo sensors with sensitivity maxima at different wavelengths can also be provided for detection of different materials. The wavelength changes can also be recorded with common appropriate spectral-sensitive devices as evaluation stage 10 (or a part thereof).

A variety of design possibilities are specified for the vessel 1 in which the high-voltage electrodes 4,5 are disposed, between which the gas discharge space 6 can be formed.

Figure 1A:
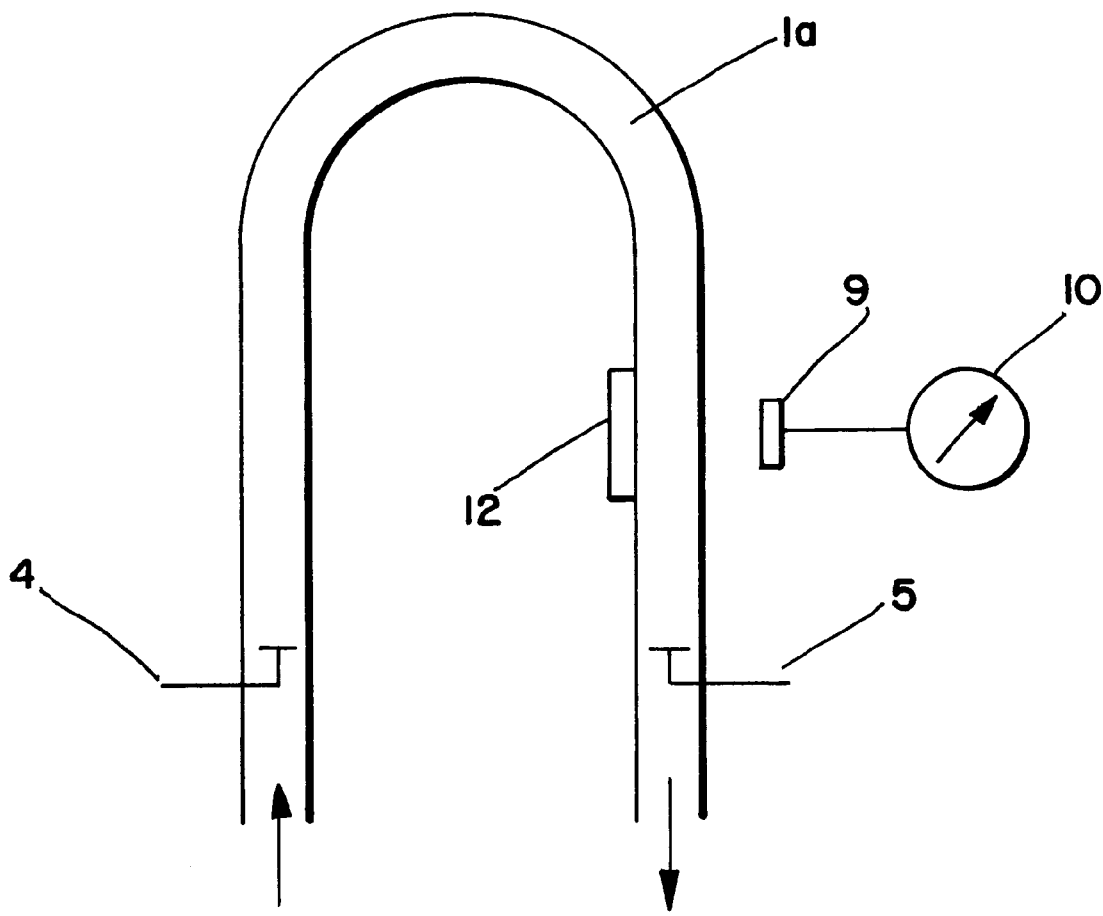

The vessel can, as shown in FIG. 1, be a straight tube, but can also, as shown in FIG. 1a, be an e.g. U-shaped bent tube 1a, which allows an especially compact shape.

Figure 1B:
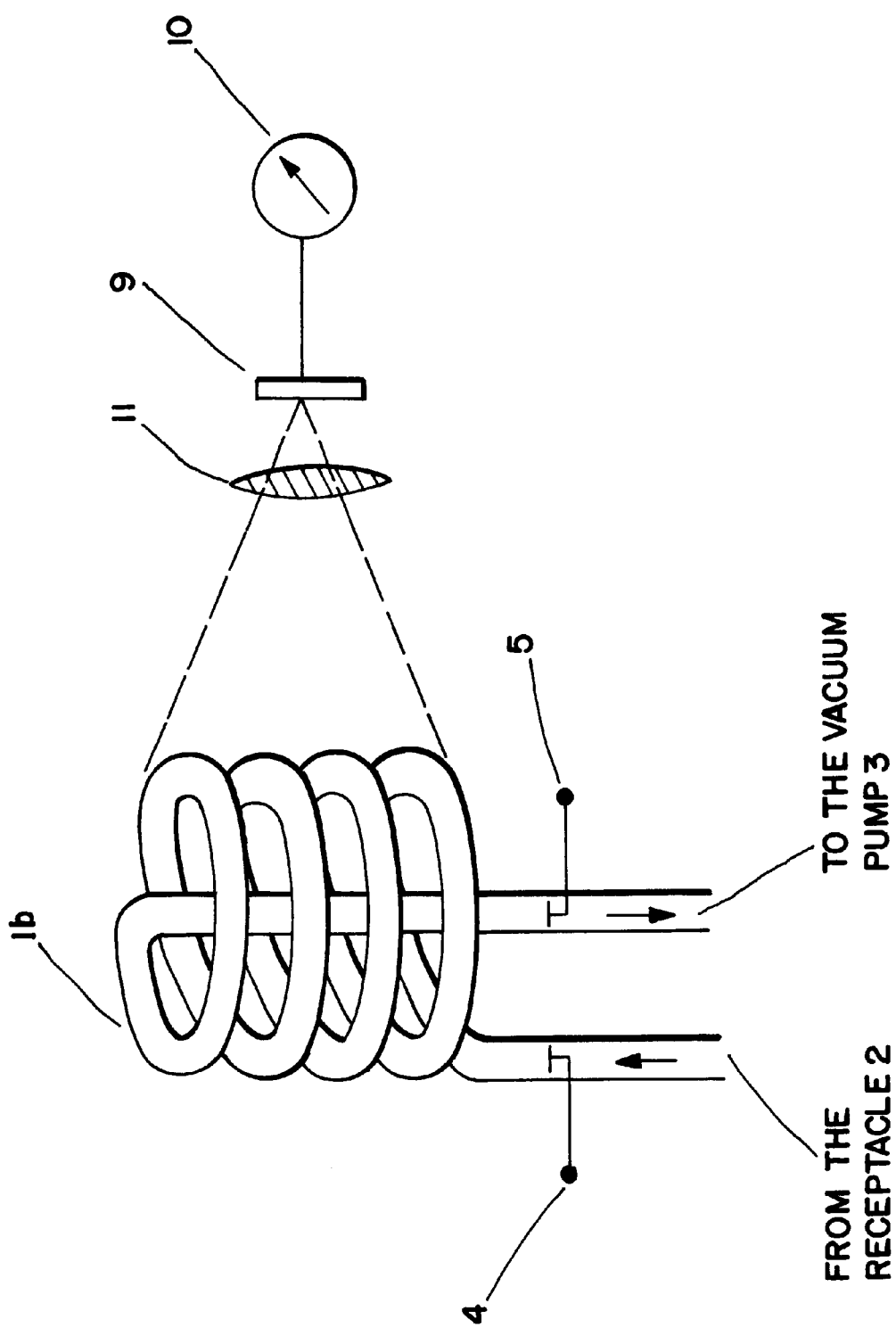

According to the embodiment shown in FIG. 1b, the vessel can also be a coiled tube 1b. Apart from a compact shape, this embodiment allows especially good exploitation of the light emission if the light is focussed in front of the photo sensor 9 by means of a suitable optical mechanism, e.g. a convergent lens 11.

FIG. 2 shows a further embodiment of the apparatus according to the invention, which differs from FIGS. 1, 1a and 1b especially by virtue of a principally different shaping of the vessel 1 and the gas discharge space 6. Similar parts are shown with the same reference characters. With the apparatus according to FIG. 2, the vessel 1 comprises two tubes 1c, 1d disposed coaxially one inside the other, which are cemented into a common metal flange 11, and of which the outer tube is closed at its free end and carries an electrode 4, which has been melted on, at its closed end; the counter-electrode 5 of FIG. 1 is formed by the metal flange 11 in this case.

The outer glass tube is closed by two ground-in ball-and-socket joint parts 12 and 13, the electrode 4 being carried by the part 13. The ground-in parts are sealed with an elastomer sealing ring 14, so that the otherwise-normal grinding lubricant can be dispensed with.

The two ground-in ball-and-socket joint parts are pressed together so as to make a vacuum-tight seal by a cap-like holder 15.

The gas stream, which is pumped by the vacuum pump 3 (not illustrated) first flows into the inner tube 1d, which is additionally cemented into a threaded sleeve 16, is then turned around at the ground ball part 13 which forms the closure, flows back through the outer tube 1c into the metal flange 11 from where it flows to the vacuum pump 3.

If, for example, small quantities of leaked material were emitted into the vacuum from the filled container 17 in the receptacle 2, which is to be tested for leaktightness, this leads to the described change in the light emission which is recorded by the photo sensor 9 and is supplied to the measuring apparatus 10 as an electrical measured value.

A computing recording comparator can be used in place of the measuring apparatus 10, this compares the electrical measured value of the photo sensor 9 with a given specified value, reaching an automatic decision on the testing process in this manner. This also applies to the embodiment according to FIG. 1.

The described embodiment according to FIG. 2 allows the apparatus to be designed very compactly in an advantageous manner, so that its installation e.g. in a machine is favoured. In addition, the measuring space can easily be dismantled for cleaning purposes.

An improvement in the light yield can be attained if the side of the vessel facing away from the photo sensor 9 is mirrored or if a separate mirror 18 is disposed on this side, as is shown by way of example in FIG. 1a. Naturally, these measures can also be correspondingly used in the case of other vessel shapes according to FIGS. 1, 1b and 2.

The detection sensitivity of the process according to the invention will be shown in the two subsequently-represented examples. In Example 1, ethanol is dosed into the vessel 1, and in Example 2 water is dosed into the vessel 1. With a pressure of 2 mbar, a voltage of 2.5 kV and a compensating resistance of 270 kΩ, the photometer signal in its starting state (only nitrogen and oxygen molecules as residual gas in a vacuum) is 9.7 V in each case (idling signal).

The absolute value of the photometer signal and the signal distance from the idling signal, i.e. the reduction in brightness, is given in each case for the respective quantities of material (doses) in the tables relating to the two examples.

A significant reduction in brightness can be seen with growing concentration of material.

EXAMPLE 1

| Quantity of ethanol dosed in the vacuum (mg/S) | Photometer signal (V) | Signal difference to idling signal (V) |
| --- | --- | --- |
| 0.008 | 9.3 | 0.4 |
| 0.015 | 8.9 | 0.8 |
| 0.025 | 8.7 | 1.0 |
| 0.120 | 7.5 | 2.2 |
| 0.210 | 5.5 | 4.2 |
| 0.330 | 3.2 | 6.5 |
| 0.430 | 2.0 | 7.7 |
| 0.450 | 1.9 | 7.8 |
| 0.470 | 1.6 | 8.1 |

EXAMPLE 2

| Quantity of water dosed in the vacuum (mg/S) | Photometer signal (V) | Signal difference to idling signal (V) |
| --- | --- | --- |
| 0.008 | 9.4 | 0.3 |
| 0.013 | 8.9 | 0.8 |
| 0.030 | 7.9 | 1.8 |
| 0.051 | 5.2 | 4.5 |
| 0.160 | 2.2 | 7.5 |
| 0.170 | 2.0 | 7.7 |
| 0.210 | 1.6 | 8.1 |
| 0.400 | 1.1 | 8.6 |
| 0.470 | 1.0 | 8.7 |

The hereinbefore-described process for non-destructively testing fluid-filled containers for leaktightness, and the associated apparatus, is especially suitable for routine examination within the framework of filling the containers. The process, according to the invention, and the associated apparatus, is here especially suitable for routine testing for leaktightness of containers which are to be filled in high unit numbers. In this way, for example, automated multiple stations, i.e. a plurality of testing chambers, connected in parallel and correspondingly equipped in parallel, or larger testing rooms can be set up as the receptacle 2 for communal acceptance of a plurality of containers. Corresponding devices which can also be evacuated are principally known from the prior art and can be adapted without problem to the apparatus in which the process according to the invention is carried out, i.e. by corresponding shaping of the connection of receptacle 2 to the gas discharge vessel 1 or 1a to 1d.

What is claimed is:

1. A process for non-destructively testing a fluid-filled container for leaktightness, the process comprising:
   (a) subjecting the fluid-filled container to a vacuum or near vacuum environment;
   (b) utilizing electrical equipment to form an electrical discharge in the vacuum or near vacuum environment sufficient to stimulate spectral light emissions from volatile fluid-filled container contents present in the vacuum or near vacuum environment;

(c) detecting the spectral light emissions from the volatile fluid-filled container contents produced in step (b); and (d) evaluating the spectral light emissions detected in step (c) to determine the amount of volatile fluid-filled container contents present in the vacuum or near vacuum environment by comparing: (i) the measured brightness level of the spectral light emissions obtained from step (c), to (ii) a base brightness level obtained by measuring the brightness level of the spectral emissions due to the presence of residual gas or air molecules in the vacuum or near vacuum environment, and analyzing the difference between the measured brightness level and the base brightness level using a corresponding empirically-determined calibration curve of brightness level to concentration of volatile container contents.

2. The process according to claim 1, wherein the electrical discharge of step (b) occurs at a pressure of between 0.5 mbar and 50 mbar.

3. The process according to claim 2, wherein the electrical discharge is driven by high-voltage electrical energy supplied by means of electrodes or capacitively or inductively.

4. The process according to claim 3, wherein the electrical discharge is driven by a high voltage selected from a DC voltage or an AC voltage with a frequency of greater than 50 kHz to 100 kHz.

5. The process according to claim 1, wherein the change in the wavelength of the spectral light emissions produced in step (b) is detected and is analyzed by comparison to spectral signatures corresponding to each of the different volatile container contents.

6. The process according to claim 2, wherein the electrical discharge of step (b) occurs at a pressure of between 1 mbar and 4 mbar.

7. The process according to claim 1, wherein the container is a fluid-filled cartridge for a propellant-free aerosol with an exchangeable storage container containing a medicament, the cartridge comprising a rigid outer container and a flexible inner container.

8. The process according to claim 1, wherein the process is performed in a product manufacturing environment as a routine examination within an assembly line process for filling containers.

9. The process according to claim 8, wherein a plurality of containers are provided in the vacuum or near vacuum environment.

10. The process according to claim 1, wherein step (c) is accomplished using a light-sensitive sensor.

11. The process according to claim 2, wherein the electrical discharge is driven by a high-voltage AC voltage with a frequency of greater than 100 kHz.

12. The process according to claim 4, wherein the electrical discharge is driven by a high-voltage AC voltage with a frequency of between 30 kHz and 40 kHz.

13. An apparatus for non-destructively testing a fluid-filled container for leaktightness, the apparatus comprising:

(a) a receptacle for holding the fluid-filled container therein and maintaining vacuum or near vacuum therein;

(b) electrical equipment for forming an electrical discharge in a gas discharge space in a vessel connected to the receptacle;

(c) a light-sensitive sensor arrangement for detecting spectral light emitted from the electrical discharge in the gas discharge space and producing a signal corresponding thereto; and (d) an evaluation circuit for evaluating the signal from the light sensitive sensor arrangement to determine the amount of volatile container contents exiting the fluid-filled container.

14. The apparatus according to claim 13, wherein the electrical equipment for forming the electrical discharge comprises a high-voltage source in which high-voltage electrical energy is supplied capacitively or inductively, or by means of electrodes, to the gas discharge space.

15. The apparatus according to claim 14, wherein the high-voltage source provides a DC voltage or an AC voltage with a frequency of 50 kHz to 100 kHz.

16. The apparatus according to claim 13, wherein the light-sensitive sensor arrangement and the evaluation circuit are designed so that changes in brightness of the emitted spectral light and/or changes in the wavelength of the emitted spectral light over a wide spectrum can be recorded and evaluated.

17. The apparatus according to claim 16, wherein the light-sensitive sensor arrangement comprises a photosensor which is wavelength-independent in a wide range of the light spectrum.

18. The apparatus according to claim 16 or 17, wherein the light-sensitive sensor arrangement is a photosensor with a specific sensitivity maximum at a specified wavelength matching the spectral light emission wavelength characteristic of the volatile container contents.

19. The apparatus according to one of claims 13 to 17, wherein the electrical equipment comprises a first electrode and a second electrode and the vessel with the gas discharge space is formed from a tube system which comprises two or more tubes arranged coaxially one inside the other such that the one end of the tubes is sealed in a metal flange which simultaneously serves as the first electrode, and the other end of the outer tube is closed with two ground-in ball-and-socket joint parts, one of which carries the second electrode.

20. The apparatus according to one of claims 13 to 17, wherein the receptacle is an evacuatable automated multiple station for parallel testing of a plurality of containers in a product manufacturing environment within the assembly line framework.

21. The apparatus according to one of claims 13 to 17, wherein the receptacle is an evacuatable large examination chamber for holding a plurality of containers in a product manufacturing environment within the assembly line framework.

22. The apparatus according to claim 14, wherein the high-voltage source provides an AC voltage with a frequency of greater than 100 kHz.

23. The apparatus according to claim 15, wherein the high-voltage source provides an AC voltage with a frequency of between 30 kHz and 40 kHz.

24. The apparatus according to claim 17, wherein the photosensor which is wavelength-independent in a wide range of the light spectrum is selected from the group consisting of a photo resistance, a photo diode, and a photo cell.

* * * * *

UNITED STATES PATENT AND TRADEMARK OFFICE
CERTIFICATE OF CORRECTION

PATENT NO. : 6,314,796 B1
DATED : November 13, 2001
INVENTOR(S) : Wittekind et al.

It is certified that error appears in the above-identified patent and that said Letters Patent is hereby corrected as shown below:

Column 1,
Line 61, "emission-spectometrically" should read -- emission-spectrometrically --.

Column 7,
Lines 29-30, "50 kHz" should read -- 50 Hz --.

Column 8,
Line 17, "50 kHz" should read -- 50 Hz --.

Signed and Sealed this

Twenty-third Day of April, 2002

Attest:

Attesting Officer

JAMES E. ROGAN
Director of the United States Patent and Trademark Office